United States Patent [19]

Berg

[11] Patent Number: 4,661,209

[45] Date of Patent: Apr. 28, 1987

[54] SEPARATION OF METHYL T-BUTYL ETHER FROM HYDROCARBONS BY EXTRACTIVE DISTILLATION

[76] Inventor: Lloyd Berg, 1314 S. Third Ave., Bozeman, Mont. 59715

[21] Appl. No.: 891,576

[22] Filed: Aug. 1, 1986

Related U.S. Application Data

[63] Continuation-in-part of Ser. No. 841,887, Mar. 20, 1986, abandoned.

[51] Int. Cl.$^4$ .......................... B01D 3/40; C07C 41/42
[52] U.S. Cl. .......................................... 203/51; 203/57; 203/58; 203/60; 203/62; 203/71; 568/699; 585/856
[58] Field of Search .................. 203/57, 51, 58, 60, 203/62, 71; 568/699, 697; 585/856, 803, 800

[56] References Cited

U.S. PATENT DOCUMENTS

| 3,689,372 | 9/1972 | Sugano | 203/57 |
| 4,148,695 | 4/1979 | Lee et al. | 568/699 |
| 4,459,178 | 7/1984 | Berg et al. | 203/57 |
| 4,510,022 | 4/1985 | Berg et al. | 203/57 |
| 4,513,153 | 4/1985 | Sandrin | 203/57 |

FOREIGN PATENT DOCUMENTS

| 3015882 | 11/1980 | Fed. Rep. of Germany | 568/699 |
| 48-00509 | 1/1973 | Japan . | |

Primary Examiner—Wilbur Bascomb

[57] ABSTRACT

Methyl t-butyl ether cannot be separated from close boiling hydrocarbons by distillation because of the proximity of their boiling points. Methyl t-butyl ether can be readily separated from close boiling hydrocarbons by using extractive distillation in which the extractive agent is higher boiling oxygenated, nitrogenous and/or sulfur containing organic compound or a mixture of two or more of these. Typical examples of effective agents are dimethylsulfoxide; dimethylsulfoxide and 2-octanone; dimethylsulfoxide, dimethylformamide and N-methyl pyrrolidone.

4 Claims, No Drawings

SEPARATION OF METHYL T-BUTYL ETHER FROM HYDROCARBONS BY EXTRACTIVE DISTILLATION

This is a continuation-in-part of Application No. 06/841,887 filed Mar. 20, 1986 and now abandoned.

FIELD OF THE INVENTION

This invention relates to a method for separating methyl t-butyl ether from hydrocarbons using certain higher boiling liquids as the extractive agent in extractive distillation.

DESCRIPTION OF PRIOR ART

Extractive distillation is the method of separating close boiling compounds by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form a minimum azeotrope with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Methyl t-butyl ether has become important commercially because of its utility as a substitute for tetra ethyl lead as an octane number enhancer in gasoline. This and other ethers are commonly produced by reacting a hydrocarbon stream containing olefins with an alcohol to form the ether. Thus the reaction product can contain a number of hydrocarbons as well as the ether. If any of these hydrocarbons boil close to the ether, separation by rectification becomes difficult to impossible depending on the proximity of the boiling points. Methyl t-butyl ether boils at 53° C. and there are several hydrocarbons that boil close to this temperature. The most commonly encountered hydrocarbon boiling in this region is cyclopentane which boils at 50° C. With a boiling point difference of only 3° C., these two are very difficult to separate. Their relative volatility is 1.2, a relationship which requires 100 theoretical plates in a rectification column to obtain 99% purity.

Extractive distillation would be an attractive method of effecting the separation of methyl t-butyl ether from hydrocarbons if agents can be found that (1) will alter the relative volatility between methyl t-butyl ether and hydrocarbons, (2) form no azeotropes with methyl t-butyl ether or hydrocarbons and (3) are easy to recover from methyl t-butyl ether, that is boil sufficiently above methyl t-butyl ether to make separation by rectification possible with only a few theoretical plates.

Extractive distillation typically requires the addition of an equal amount to twice as much extractive agent as the methyl t-butyl ether-hydrocarbons on each plate in the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. Twenty Centigrade degrees or more difference is recommended. It is also desirable that the extractive agent be miscible with methyl t-butyl ether otherwise it will form a two phase azeotrope with the methyl t-butyl ether in the recovery column and some other method of separation will have to be employed.

Vu Pre Petrochemiu, German Patent No. 3015-882, Nov. 6, 1980, described the use of ethylene glycol, propylene glycol, glycerol, ethanolamine, isopropanolamine and dimethylformamide used individually as the extractive distillation agent to separate methyl t-butyl ether from methanol, water and/or hydrocarbons.

OBJECTIVE OF THE INVENTION

The object of this invention is to provide a process or method of extractive distillation that will enhance the relative volatility of hydrocarbons from methyl t-butyl ether in their separation in a rectification column. It is further objective of this invention to identify organic compounds which are stable, can be separated from methyl t-butyl ether by rectification with relatively few plates and can be recycled to the extractive distillation column and re-used with little decomposition.

SUMMARY OF THE INVENTION

The objects of this inention are provided by a process for separating cyclopentane (CP) from methyl t-butyl ether (MTBE) which entails the use of certain oxygenated, nitrogenous and/or sulfur containing organic compounds as the agent in extractive distillation.

DETAILED DESCRIPTION OF THE INVENTION

I have discovered that certain oxygenated, nitrogenous and/or sulfur containing organic compounds will effectively enhance the relative volatility between cyclopentane (CP) and methyl t-butyl ether (MTBE) and permit the separation of CP from MTBE by rectification when employed as the agent in extractive distillation. Table 1 lists dimethylsulfoxide and its mixtures and approximate proportions that I have found to be effective. The data in Table 1 was obtained in a vapor-liquid equilibrium still. In each case, the starting material was a 10%–90% CP-MTBE mixture because this is the usual combination occuring in commercial production. The ratios are the parts of extractive agent used per part of CP-MTBE mixture.

The compound that is effective as an extractive distillation agent when used alone is dimethylsulfoxide (DMSO). The compounds which are effective when used in mixtures of two or more components with DMSO are acetophenone, 2-octanone, benzophenone, N,N-dimethyl-acetamide, dimethylformamide, methyl glutaronitrile, propiophenone, N-methyl pyrrolidone, acetamide, diisobutyl ketone, ethylene glycol butyl ether acetate, ethylene glycol ethyl ether acetate and hexylene glycol diacetate. The ratios in Table 1 are the parts of extractive agent used per part of CP-MTBE mixture. For example in Table 1, one part of DMSO with one part of CP-MTBE mixture gives a relative volatility of 8.9. One half part of DMSO mixed with one half part of 2-octanone with one part of CP-MTBE mixture gives a relative volatility of 9.1. One third parts of DMSO plus ⅓ parts of dimethylformamide plus ⅓ parts of N-methyl pyrrolidone mixed with one part of CP-MTBE mixture gives a relative volatility of 16.8. In every example in Table 1 the starting material is a 10–90% mixture of CP-MTBE which possesses a relative volatility of 1.2.

The DMSO, DMFA, acetamide mixture listed in Table 1 and whose relative volatility had been determined in the vapor-liquid equilibrium still, was then evaluated in a glass perforated plate rectification column possessing 4.5 theoretical plates. The results are listed in Table 2. The CP-MTBE mixture used contained 6% CP, 94% MTBE. The first line in Table 2 is the result obtained after one hour operation with from one to two parts of extractive agent per part of CP-MTBE mixture being boiled up to the condenser.

TABLE 1

Extractive Distillation Agents Containing Dimethylsulfoxide.

| Compounds | Ratio | Relative Volatility |
|---|---|---|
| None | — | 1.2 |
| Dimethylsulfoxide (DMSO) | 2 | 8.9 |
| DMSO, Dimethylformamide (DMFA) | (½)² | 13.2 |
| DMSO, Diisobutylketone | " | 4.1 |
| DMSO, Ethylene glycol ethyl ether acetate | " | 4.0 |
| DMSO, N—Methylpyrrolidone | " | 8.0 |
| DMSO, 2-Octanone | " | 9.1 |
| DMSO, DMFA, Acetamide | (⅓)³ | 5.5 |
| DMSO, DMFA, Acetophenone | " | 4.9 |
| DMSO, DMFA, Benzophenone | " | 7.7 |
| DMSO, DMFA, Diisobutyl ketone | " | 4.8 |
| DMSO, DMFA, N,N—Dimethyl acetamide | " | 4.6 |
| DMSO, DMFA, Ethylene glycol butyl ether acetate | " | 4.8 |
| DMSO, DMFA, Ethylene glycol ethyl ether acetate | " | 4.3 |
| DMSO, DMFA, Hexylene glycol diacetate | " | 6.7 |
| DMSO, DMFA, Methyl glutaronitrile | " | 11.9 |
| DMSO, DMFA, N—Methyl pyrrolidone | " | 16.8 |
| DMSO, DMFA, Propiophenone | " | 7.0 |

The second line is the result after 1.5 hours which is usually the maximum time required for the equipment to come to equilibrium. The third line is the result after two hours of total operating time and indicates that equilibrium through-out the column has been achieved.

THE USEFULNESS OF THE INVENTION

The usefulness or utility of this invention can be demonstrated by referring to the data presented in Tables 1 and 2. All of the successful extractive distillation agents show that CP can be removed from MTBE by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity cyclopentane and methyl t-butyl ether from any mixture of these two. The stability of the compounds used and the boiling point difference is such that complete recovery and recycle is obtainable by a simple distillation and the amount required for make-up is small.

WORKING EXAMPLES

EXAMPLE 1

Five grams of cyclopentane (CP), 45 grams of methyl t-butyl ether (MTBE) and fifty grams of dimethylsulfoxide (DMSO) were charged to an Othmer type glass vapor-liquid equilibrium still and refluxed for three hours. Analysis of the vapor and liquid by gas chromatography gave vapor composition of 24.5% CP, 75.5% MTBE and a liquid composition of 3.5% CP, 96.5% MTBE. This indicates a relative volatility of 8.9.

EXAMPLE 2 Fifty grams of the CP-MTBE mixture, 25 grams of DMSO and 25 grams of 2-octanone were charged to the vapor-liquid equilibrium still and refluxed for six hours. Analysis indicated a vapor composition of 14.2% CP, 85.8% MTBE; a liquid composition of 1.7% CP, 98.3% MTBE which is a relative volatility of 9.1.

EXAMPLE 3

Fifty grams of the CP-MTBE mixture, 17 grams of DMSO 17 grams of dimethylformamide and 17 grams of N-methyl pyrrolidone were charged to the vapor-liquid equilibrium still and refluxed for eight hours. Analysis indicated a vapor composition of 17.7% CP, 82.3% MTBE and a liquid composition of 1.6% CP, 98.4% MTBE which is a relative volatility of 16.8.

EXAMPLE 4

A glass perforated plate rectification column was calibrated with ethylbenzene and p-xylene which possesses a relative volatility of 1.6 and found to have 4.5 theoretical plates. A solution of 40 grams of CP and 360 grams of MTBE was placed in the stillpot and heated. When refluxing began, an extractive agent consisting of 33.3% each of DMSO, DMFA and acetamide was pumped into the column at a rate of 20 ml/min. The temperature of the extractive agent as it entered the

TABLE 2

Data From Run Made In Rectification Column at 630 mm. Hg.

| Agent | Time min. | Overhead Temp. °C. | Stillpot Temp., °C. At Start | Stillpot Temp., °C. When Sampling | Weight % Cyclopentane Overhead | Weight % Cyclopentane Bottoms | Relative Volatility |
|---|---|---|---|---|---|---|---|
| DMSO, DMFA, Acetamide | 60 | 45 | 49 | 60 | 99.4 | 5.5 | 5.7 |
| " | 90 | 44.5 | 49 | 64 | 99.5 | 6.0 | 5.9 |
| " | 120 | 44.5 | 49 | 68 | 99.5 | 6.1 | 5.95 |
| | | | | | | Average | 5.85 | column was 40° C. After establishing the feed rate of the extractive agent, the heat input of the CP-MTBE in the stillpot was adjusted to give a reflux rate of 10–20 ml/min. After one hour of operation, overhead and bottoms samples of approximately two ml. were collected and analysed using gas chromatography. The overhead analysis was 99.4% CP, 0.6% MTBE. The bottoms analysis was 5.5% CP, 94.5% MTBE. Using these compositions in the Fenske equation, with the number of theoretical plates in the column being 4.5, gave an average relative volatility of 5.7 for each theoretical plate. After 1.5 hours of total operating time, the overhead and bottoms samples were again taken and analysed. The overhead composition was 99.5% CP, 0.5% MTBE and the bottoms composition was 6% CP and 94% MTBE. This gave an average relative volatility of 5.9 for each theoretical plate. After two hours of total operating time, the overhead and bottoms samples were again taken and analysed. The overhead composition was 99.5% CP, 0.5% MTBE and the bottoms composition was 6.1% CP, 93.9% MTBE. This gave an average relative volatility of 5.95 for each theoretical plate.

What is claimed is:

1. A method for recovering methyl t-butyl ether from a mixture of methyl t-butyl ether and close boiling hydrocarbons which comprises distilling a mixture of methyl t-butyl ether and close boiling hydrocarbons in a rectification column in the presence of about one to two parts of extractive agent per part of methyl t-butyl ether-close boiling hydrocarbon mixture, recovering the hydrocarbons as overhead product, obtaining the methyl t-butyl ether and the extractive agent from the stillpot, separating the methyl t-butyl ether from the extractive agent by distillation in another rectification column, wherein said extractive agent is dimethylsulfoxide.

2. The method of claim 1 in which the extractive agent comprises dimethylsulfoxide and at least one material from the group consisting of acetophenone, 2-octanone, benzophenone, acetamide, N,N-dimethylacetamide, dimethylformamide, methyl glutaronitrile, propiophenone, N-methyl pyrrolidone, diisobutyl ketone, ethylene glycol butyl ether acetate, ethylene glycol ethyl ether acetate and hexylene glycol diacetate.

3. The method of claim 1 in which the close boiling hydrocarbon is cyclopentane.

4. The method of claim 2 in which the close boiling hydrocarbon is cyclopentane.

* * * * *